(12) United States Patent (10) Patent No.: US 12,685,508 B2

Melodelima et al. (45) Date of Patent: Jul. 21, 2026

(54) METHODS AND SYSTEMS FOR ALIGNING AN IMAGING ULTRASOUND PROBE WITH A THERAPEUTIC ULTRASOUND PROBE

(71) Applicants:INSTITUT NATIONAL DE LA SANTE ET DE LA RECHERCHE MEDICALE, Paris (FR); CENTRE LEON BERARD, Lyons (FR); UNIVERSITÉ CLAUDE BERNARD LYON 1, Villeurbanne (FR)

(72) Inventors: David Melodelima, Lyons (FR); Sophie Cambronero, Lyons (FR)

(73) Assignees: INSERM (INSTITUT NATIONAL DE LA SANTE ET DE LA RECHERCHE MEDICALE), Paris (FR); CENTRE LEON BERARD, Lyons (FR); UNIVERSITÉ CLAUDE BERNARD LYON 1, Villeurbanne (FR)

( * ) Notice: Subject to any disclaimer, the term of this patent is extended or adjusted under 35 U.S.C. 154(b) by 0 days.

(21) Appl. No.: 18/853,258

(22) PCT Filed: Apr. 7, 2023

(86) PCT No.: PCT/EP2023/059323

§ 371 (c)(1),
(2) Date: Oct. 1, 2024

(87) PCT Pub. No.: WO2023/194610

PCT Pub. Date: Oct. 12, 2023

(65) Prior Publication Data

US 2025/0213217 A1    Jul. 3, 2025

(30) Foreign Application Priority Data

Apr. 7, 2022    (EP) ..................................... 22305481

(51) Int. Cl.
*A61B 8/00* (2006.01)

(52) U.S. Cl.
CPC ............ *A61B 8/4263* (2013.01); *A61B 8/463* (2013.01)

(58) Field of Classification Search
CPC ..... A61B 8/4263; A61B 8/463; A61B 8/4218; A61B 8/4444; A61B 8/4455; A61N 2007/0091; A61N 2007/0095; A61N 7/02
See application file for complete search history.

(56) References Cited

U.S. PATENT DOCUMENTS

2005/0240126 A1* 10/2005 Foley ....................... A61B 8/06
                                                        601/2
2013/0172739 A1* 7/2013 Paladini ............... A61B 6/5247
                                                        601/2

(Continued)

*Primary Examiner* — Alexei Bykhovski
(74) *Attorney, Agent, or Firm* — WCF IP

(57) ABSTRACT

Devices and methods using high intensity focused ultra-sounds (HIFU) guided by ultrasound imaging often require an imaging ultrasound probe to be embedded within a HIFU transducer, in order for both probes to have a substantially similar position during operation. This configuration has many drawbacks and often causes poor imaging conditions due to constraints on the size of the imaging probe. The new methods and systems described herein allow the use of an imaging ultrasound probe separate from the HIFU transducer. The imaging ultrasound probe can be easily positioned relative to the HIFU transducer during operation by using a position capture system and a specific housing for the imaging probe. The invention is also applicable to high intensity contact ultrasound probes (HICU).

15 Claims, 4 Drawing Sheets

(56)        References Cited

U.S. PATENT DOCUMENTS

2013/0237811 A1      9/2013  Mihailescu et al.
2014/0316269 A1*  10/2014  Zhang ................. A61B 8/4209
                                                    602/1
2020/0069976 A1*   3/2020  Puleo .................... A61B 90/37
2022/0313211 A1*  10/2022  Eltorai ................. A61B 8/462

* cited by examiner

METHODS AND SYSTEMS FOR ALIGNING AN IMAGING ULTRASOUND PROBE WITH A THERAPEUTIC ULTRASOUND PROBE

TECHNICAL FIELD

The present disclosure relates to ultrasonic transducers.

BACKGROUND

Therapeutic ultrasound techniques, such as high-intensity focused ultrasound (HIFU) techniques, are increasingly used in a wide range of applications as a non-invasive method for destroying targets, such as tumors, in biological tissues or organisms.

Generally, one or more HIFU transducers are used to generate an ultrasound beam directed towards a target located inside a biological tissue or organism. The ultrasound beam generates waves of mechanical pressure at specific locations inside the biological tissue, which result in a local increase of temperature, leading to the destruction of the target.

Usually, the target region is imaged with an ultrasound imaging probe before destroying the target with HIFU beams emitted by the HIFU transducers. To that end, therapeutic HIFU probes are often used in conjunction with imaging ultrasound probes.

In many cases, the ultrasonic imaging probe is embedded in the HIFU probe and is usually placed at or near the center of the HIFU transducer in a combined probe.

This configuration allows the imaging probe to be positioned at the same location as the HIFU transducer during operation, in such a way that the emission axis of the HIFU transducer is aligned with the emission axis of the imaging probe.

A drawback of this configuration is that the imaging probe must be small to be placed near or at the center of the HIFU transducer, in order to avoid increasing the size and degrading the performances of the HIFU transducer.

However, reducing the size of the imaging probe may degrade the imaging capabilities of the imaging probe. In some cases, for example when the target region is a biological organ located deep in the body, such as a liver or a kidney, a small imaging probe can be unable to obtain a proper image of the organ, which can lead to a failure of the treatment or may compromise the precision of the treatment.

Thus, an unsatisfactory compromise has to be found between the performances of the HIFU transducer and the imaging probe.

Moreover, in the configuration as described above, the HIFU transducer is in contact with the body (e.g. in direct contact with the skin) but the imaging probe is placed at a distance from the tissue and is separated from the body by a water gap and/or a gel gap, due to the shape of the combined probe. As a consequence, the image quality is also strongly affected by artefacts due to interfaces reflections caused by the absence of direct contact.

There is therefore a need for ultrasonic imaging probes and HIFU transducers capable of overcoming at least some of the aforementioned drawbacks.

SUMMARY

An object of the present invention is therefore to provide a method for positioning a therapeutic ultrasonic probe relative to an imaging ultrasonic probe, the method comprising, by an electronic control device:

acquiring the position of a first probe chosen among the ultrasonic imaging probe and the therapeutic ultrasonic probe, the position being acquired with a position capture system when the first probe is in a first position, the ultrasonic imaging probe being placed inside a housing, the housing comprising at least one position marker detectable by the position capture system, the external dimensions of the housing having being similar to the external dimensions of the therapeutic ultrasonic probe, detecting the position of a second probe chosen among the other of the ultrasonic imaging probe and the therapeutic ultrasonic probe, the position being detected using the position capture system, the therapeutic ultrasonic probe comprising at least one position marker detectable by the position capture system, indicating the target position of the second probe based on the acquired position of the first probe.

In some optional embodiments, the first probe is the ultrasonic imaging probe, wherein the second probe is the therapeutic ultrasonic probe, and wherein the first position is an imaging position.

In some optional embodiments, the first probe is the therapeutic ultrasonic probe, wherein the second probe is the ultrasonic imaging probe, and wherein the first position is a target position.

In some embodiments, each of the therapeutic ultrasonic probe and the ultrasonic imaging probe have an ultrasound emission axis, and the target position also comprises indicating a direction of the ultrasound emission axis.

In some optional embodiments, the system is configured to provide positioning data to an operator tasked with positioning the second probe.

In some optional embodiments, indicating the target position of the therapeutic ultrasonic probe comprises visually displaying the current position of the therapeutic ultrasonic probe and the target position of the therapeutic ultrasonic probe on a graphical user interface connected to the electronic control device.

In some optional embodiments, indicating the target position of the therapeutic ultrasonic probe comprises emitting an auditory feedback depending on the difference between the current position of the therapeutic ultrasonic probe and the target position of the therapeutic ultrasonic probe.

In some optional embodiments, indicating the target position of the therapeutic ultrasonic probe comprises emitting a haptic feedback depending on the difference between the current position of the therapeutic ultrasonic probe and the target position of the therapeutic ultrasonic probe.

In some optional embodiments, the therapeutic ultrasonic probe is held by a robot, and wherein indicating the target position of the therapeutic ultrasonic probe comprises sending position instructions to an electronic controller of the robot, the position instructions being configured to cause the robot to place the therapeutic ultrasonic probe at the desired position.

According to another aspect, the invention relates to a system for positioning a therapeutic ultrasonic probe relative to an imaging ultrasonic probe, comprising a therapeutic ultrasonic probe, an imaging ultrasonic probe placed inside a housing, a position capture system and an electronic control device, wherein the external dimensions of the imaging probe housing being similar to the external dimensions of the therapeutic ultrasonic probe, wherein the housing comprises at least one position marker detectable by the position capture system, wherein the therapeutic ultrasonic probe comprises at least one position marker detectable by the position capture system, and wherein the electronic control device is configured to:

acquire the position of a first probe chosen among the ultrasonic imaging probe and the therapeutic ultrasonic probe with the position capture system when the first probe is in a first position, detect the position of a second probe chosen among the other of the ultrasonic imaging probe and the therapeutic ultrasonic probe, using the position capture system, indicate a target position of the second probe based on the acquired position of the first probe.

According to another aspect, the invention relates to a system for positioning a therapeutic ultrasonic probe relative to an imaging ultrasonic probe, comprising a therapeutic ultrasonic probe, an imaging ultrasonic probe placed inside a housing, a position capture system and an electronic control device, wherein the housing has the same external dimensions as the therapeutic ultrasonic probe and comprises at least one position marker detectable by the position capture system, wherein the therapeutic ultrasonic probe comprises at least one position marker detectable by the position capture system, and wherein the electronic control device is configured to:

acquire the position of the ultrasonic imaging probe with a position capture system when the ultrasonic imaging probe is in an imaging position, detect the position of the therapeutic ultrasonic probe using the position capture system, indicating the target position of the therapeutic ultrasonic probe based on the acquired position of the ultrasonic imaging probe.

In some optional embodiments, the system comprises a graphical user interface connected to the electronic control device and wherein indicating the target position of the therapeutic ultrasonic probe comprises visually displaying the current position of the therapeutic ultrasonic probe and the target position of the therapeutic ultrasonic probe on the graphical user interface.

In some optional embodiments, indicating the target position of the therapeutic ultrasonic probe comprises emitting an auditory feedback depending on the difference between the current position of the therapeutic ultrasonic probe and the target position of the therapeutic ultrasonic probe.

In some optional embodiments, indicating the target position of the therapeutic ultrasonic probe comprises emitting a haptic feedback depending on the difference between the current position of the therapeutic ultrasonic probe and the target position of the therapeutic ultrasonic probe.

In some optional embodiments, the system comprises a robot configured to hold the imaging probe, and wherein indicating the target position of the therapeutic ultrasonic probe comprises sending position instructions to an electronic controller of the robot, the position instructions being configured to cause the robot to place the therapeutic ultrasonic probe at the desired position.

In some optional embodiments, the imaging probe is received in a reception portion of the housing and wherein the housing comprises a mobile element configured to modify the size of the reception portion.

In some optional embodiments, the housing comprises a secondary reception portion for receiving removable weights.

In some optional embodiments, the position markers of the therapeutic probe are placed at the same relative positions as the position markers of the housing.

In some optional embodiments, the housing is made of a biocompatible material.

In some optional embodiments, the position markers are optical position markers, the position capture system comprising at least one image sensor.

In some optional embodiments, the position markers are magnetic position markers, the position capture system comprising at least one magnetic sensor.

In some optional embodiments, the position markers are radiofrequency position markers, the position capture system comprising at least one radiofrequency sensor.

BRIEF DESCRIPTION OF THE DRAWINGS

The invention will be understood upon reading the following description, provided solely as an example, and made in reference to the appended drawings, which may not necessarily be to scale and in which certain features of the disclosure may be shown in somewhat schematic form.

DETAILED DESCRIPTION OF SOME EMBODIMENTS

Figure 1:
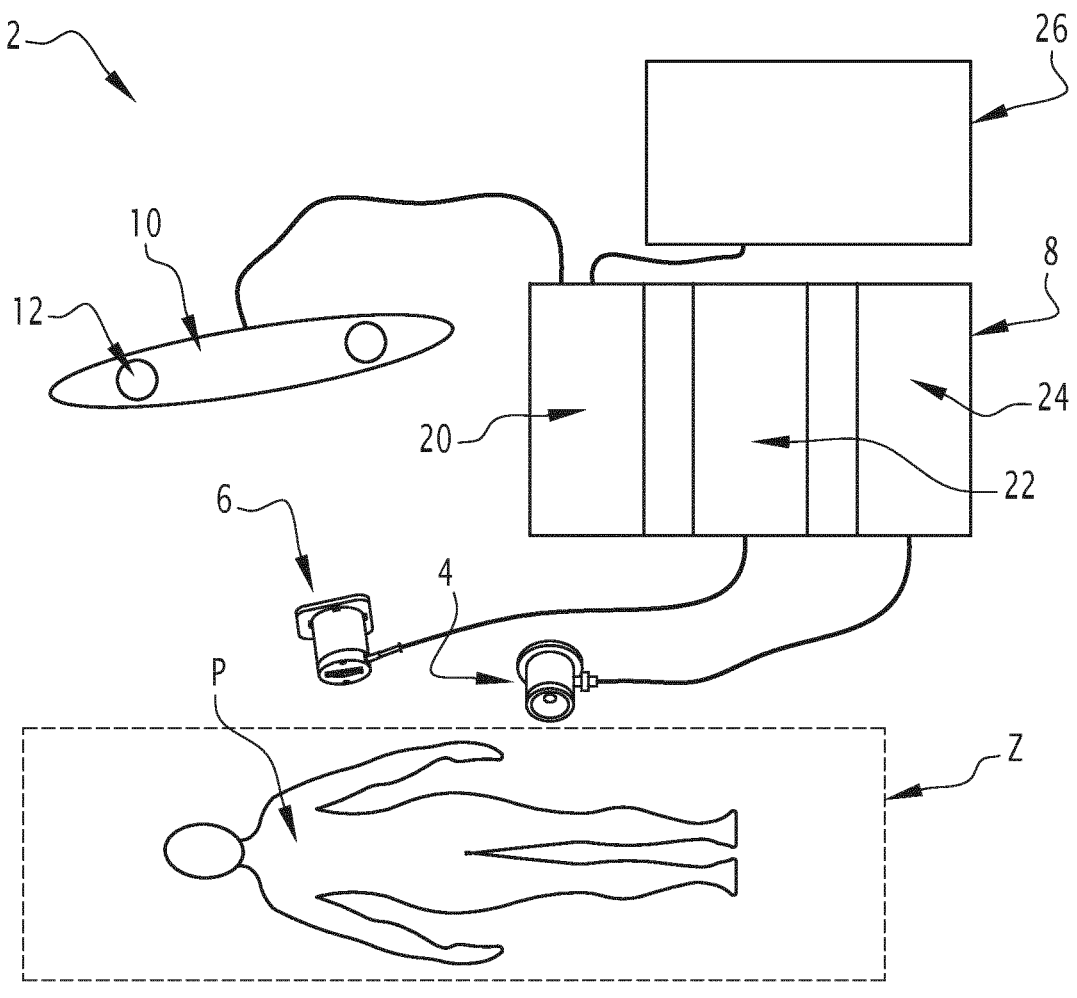
FIG. 1 is a simplified diagram of a system according to a first embodiment of the invention.

On FIG. 1 there is illustrated a system 2 comprising: a therapeutic ultrasonic probe 4, which may also be designated as ultrasonic therapeutic probe hereafter; an imaging ultrasonic probe 6, which may also be designated as ultrasonic imaging probe hereafter, placed inside a housing; an electronic control device 8 and a position capture system 10.

For example, the position capture system 10 comprises at least one sensor 12 for detecting the position of an object comprising one or more position markers.

The therapeutic ultrasonic probe 4 comprises at least one position marker detectable by the position capture system 10. The housing of the imaging ultrasonic probe 6 also comprises at least one position marker detectable by the position capture system 10.

Preferably, the therapeutic ultrasonic probe 4 and the imaging ultrasonic probe 6 comprise the same number of position markers. Preferably, the position markers are identical or similar.

The therapeutic ultrasonic probe 4 and the imaging ultrasonic probe 6 are then said to be in the same or essentially the same position when respective position markers of the therapeutic ultrasonic probe 4 and the imaging ultrasonic probe 6 are placed at the same or essentially the same spatial position, within a margin of error.

In the illustrated example, the electronic control device 8 comprises a processor 20, an acquisition interface 22 (such as an ultrasound imaging scanner) and an output driver 24 (such as a power amplifier).

The electronic control device 8 can also comprise (or be connected to) a user interface device 26. The user interface device 26 may comprise a display screen and/or a sound source and/or input devices, such as a keyboard, a mouse, a pointer, a touchscreen, or any suitable device. The user interface device 26 also comprises (or is connected to, or is at least operatively coupled to) a graphical display. For example, the graphical display of the interface 26 may comprise a computer monitor, or a television screen, or a touch-sensitive screen, or a handheld computing device comprising a display screen (e.g., a smartphone), or a wearable computing device comprising a display screen, or a virtual reality display, or an augmented reality display, or a holographic display system, or any equivalent graphical display system, or any combination thereof.

The therapeutic ultrasonic probe 4 and the imaging ultrasonic probe 6 are connected to the electronic control device 8 (e.g. to the acquisition interface 22 and the output driver 24, respectively).

In this disclosure, the expression "processor" refers not only to electronic controller devices including a microprocessor or a microprocessor, but also refer to other equivalent elements such as programmable logic controllers (PLC), application-specific integrated (ASIC) circuits, digital signal processors (DSP), graphical processor units (GPU), field-programmable gate array (FGPA) circuits, logic circuits, analog circuitry, equivalents thereof, and any other circuit or processor capable of executing the functions described herein. For example, the electronic control device 8 is a personal computer (PC) such as a workstation or a laptop computer.

The therapeutic ultrasonic probe 4 comprises a high-intensity ultrasound transducer capable of emitting a high-intensity ultrasound beam.

In many preferred embodiments, the therapeutic ultrasonic probe 4 comprises a high-intensity focused ultrasound transducer (HIFU) capable of emitting a high-intensity focused ultrasound beam.

In other embodiments, the therapeutic ultrasonic probe 4 comprises a high-intensity contact ultrasound transducer (HICU) capable of emitting a high-intensity ultrasound beam. This category of transducer may include plane wave ultrasound transducers or divergent ultrasound transducers.

In some applications, the high-intensity ultrasound beam (and preferably the high-intensity focused ultrasound beam) may be used to destroy a target located in a biological tissue or an organism.

The imaging ultrasonic probe 6 is capable of imaging a target region (e.g. acquiring an ultrasound mapping of the target region) by means of ultrasonography techniques, such as Doppler ultrasonography. For example, the imaging ultrasonic probe 6 comprises an ultrasonic transducer capable of emitting and detecting ultrasound waves. The electronic control device 8 is configured to generate an ultrasound mapping from the signals measured by the imaging ultrasonic probe 6 e.g. using suitable signal processing algorithms.

For example, the therapeutic ultrasonic probe 4 and the imaging ultrasonic probe 6 are commercially available ultrasonic probes.

The difference between imaging (or diagnosis) ultrasound probes and therapeutic ultrasound probes is well known. In practice, the amplitude of the ultrasounds waves emitted by the imaging ultrasonic probe 6 is lower than that of the ultrasound beams emitted by the therapeutic ultrasonic probe 4. For example, the therapeutic ultrasonic probe 4 and the imaging ultrasonic probe 6 each comprise a piezoelectric element capable of vibrating at a resonant frequency, the quality factor of the piezoelectric element of the therapeutic ultrasonic probe 4 being higher than the quality factor of the piezoelectric element of the imaging ultrasonic probe 6.

The system 2 can be used for therapeutic applications, e.g. on the human body or on an animal body. However, in alternative embodiments, the system 2 can be used in other applications, e.g. in industrial applications for example to modify structural properties of materials such as soft materials (e.g. polymers).

In the illustrated example, the system 2 can be used on a subject P, such as a human subject (e.g. a human patient) or an animal subject, preferably a living subject. The subject P is not part of the system 2. The reference Z depicts a target zone associated to the subject P.

In many embodiments, the imaging ultrasonic probe 6 is preferably used in conjunction with the therapeutic ultrasonic probe 4. An image of a target region is acquired by the imaging ultrasonic probe 6 before destroying the target with the therapeutic ultrasonic probe 4.

In other words, the imaging ultrasonic probe 6 and the therapeutic ultrasonic probe 4 are preferably used sequentially.

During operation, the imaging ultrasonic probe 6 and the therapeutic ultrasonic probe 4 must be successively placed at a same position or essentially the same position and (once placed each after another at said position) must have their ultrasound emission axis aligned or essentially aligned in the same direction. For example, the respective ultrasound emission axes of the imaging ultrasonic probe 6 and the therapeutic ultrasonic probe 4 must be pointed towards the target to be imaged and/or destroyed.

For example, in the present disclosure, the ultrasound emission axis of the imaging ultrasonic probe 6 and the therapeutic ultrasonic probe 4 are said to be "aligned or essentially aligned" when the axes are aligned along the same direction within an angle of ±5 degrees or ±10 degrees.

For example, in this disclosure, the imaging ultrasonic probe 6 and the therapeutic ultrasonic probe 4 are said to be at a "same position or essentially the same position" when both probes are placed at a same spatial position within an error margin that depends on the volume of treatment (i.e. the volume in which the therapeutic dose is delivered by the therapeutic ultrasound probe). Depending on application and intended uses, the error margin may be equal to or lower than 20%, or equal to or lower than 10%. In other words, the tolerable error margin on the position between the probes 4 and 6 is lower in applications for which a higher precision is required.

For example, in applications in which the target region is in a critical organ, such as is brain tissue, then a submillimeter precision is required, and thus the ultrasonic probe 6 and the therapeutic ultrasonic probe 4 are said to be "aligned or essentially aligned" when their respective position differ by at most ±1 millimeter.

In other applications, for example when the target region is liver tissue, then a coarser precision can be tolerated, and thus the ultrasonic probe 6 and the therapeutic ultrasonic probe 4 are said to be at the "same position or essentially the same position" when their respective position differ by at most ±1 centimeter or lower.

An objective of the invention is to facilitate the positioning of the therapeutic ultrasonic probe 4 at the same position or essentially the same position as the imaging ultrasonic probe 6 and with the same alignment or essentially the same alignment (e.g., aligned within an angle of ±5 degrees or ±10 degrees).

In preferred embodiments, the electronic control device 8 is configured to:

acquire the position of the ultrasonic imaging probe 6 with a position capture system when the ultrasonic imaging probe is in an imaging position (e.g. pointed towards a target region), for example during an imaging step during which the ultrasonic imaging probe 6 images the target region, detect the position of the therapeutic ultrasonic probe 4 using the position capture system (e.g. after the ultrasonic imaging probe 6 has been removed once the imaging step has been completed and the therapeutic ultrasonic probe 4 has been acquired by the operator), indicate the target position of the therapeutic ultrasonic probe 4 based on the acquired position of the ultrasonic imaging probe.

In particular, the target position of the therapeutic ultrasonic probe 4 is the same or essentially the same as the acquired position of the ultrasonic imaging probe, including the same or essentially the same spatial position and direction of the ultrasound emission axis. Advantageously, it is then ensured that the therapeutic ultrasonic probe 4 reaches the target precisely located using the ultrasonic imaging probe 6, even though the ultrasonic imaging probe 6 and the therapeutic ultrasonic probe 4 are successively applied. More generally, the electronic control device 8 is configured to:

acquire the position of a first probe chosen among the ultrasonic imaging probe 6 and the therapeutic ultrasonic probe 4, the position being acquired with a position capture system when the first probe is in a first position, the ultrasonic imaging probe being placed inside a housing, the housing comprising at least one position marker detectable by the position capture system, the external dimensions of the housing being similar to the external dimensions of the therapeutic ultrasonic probe, detect the position of a second probe chosen among the of the ultrasonic imaging probe and the therapeutic ultrasonic probe (the second probe being different from the first probe), the position being detected using the position capture system, the therapeutic ultrasonic probe comprising at least one position marker detectable by the position capture system, indicate the target position of the second probe based on the acquired position of the first probe.

For example, the invention is applicable in embodiments in which a practitioner or operator may prefer to first place the therapeutic ultrasonic probe 4 at the target location, and then place the ultrasonic imaging probe 6 to image the area in order to confirm whether the therapeutic ultrasonic probe 4 was positioned correctly. In particular, such an embodiment may be envisaged in the case when the therapeutic ultrasonic probe 4 also comprises an imaging probe, for example placed near or at the center of the HIFU transducer, which is small and does not provide a proper image of the target region, but provides however a first image or first images of the target region. In such a case, the practitioner may envisage placing firstly the therapeutic ultrasonic probe 4 using the first image(s) at a first target position, and then removing the therapeutic ultrasonic probe 4 to place the ultrasonic imaging probe 6, so as to acquire a more precise image of the target region, and therefore to validate the first target position or otherwise to acquire a second target position. In that case, the first probe is the therapeutic ultrasonic probe 4, the second probe is the ultrasonic imaging probe 6, and the first position of the therapeutic ultrasonic probe is a target position (e.g., a target of the zone to be destroyed by the high intensity ultrasound beam), as initially envisaged, also called first target position.

Alternatively, the first image or images may be provided by a different imaging system.

The second probe is then placed in the first target position, so as to check whether the first target position is a correct target position with respect to the zone to be destroyed. If however the first target position is a correct target position with respect to the zone to be destroyed, the process as described above is carried out, wherein the ultrasonic imaging probe 6 is the first probe and the therapeutic ultrasonic probe 4 is the second probe.

In other words, in some embodiments the electronic control device 8 is configured to:

acquire a first target position of the therapeutic ultrasonic probe 4 using a first image of a target region, the first target position being acquired with the position capture system 10, the therapeutic ultrasonic probe 4 comprising at least one position marker detectable by the position capture system, detect the position of the ultrasonic imaging probe 6 using the position capture system 10, the ultrasonic imaging probe being placed inside a housing, the housing comprising at least one position marker detectable by the position capture system 10, the external dimensions of the housing being similar to the external dimensions of the therapeutic ultrasonic probe 4, indicate the first target position of the therapeutic ultrasonic probe 4 to position the ultrasonic imaging probe 6 at said first target position, and provide at least a second image of the target region by the ultrasonic imaging probe 6;

acquire a second target position using the second image of the target region.

In some embodiments, as illustrated in FIG. 1, the system 2 is configured to facilitate the positioning of the therapeutic ultrasonic probe 4 by indicating a target position of the therapeutic ultrasonic probe to an operator (e.g. a human operator) manually handling the therapeutic ultrasonic probe 4, by means of a continued and/or guided human-machine interaction process. Preferably, the target position corresponds to a previously acquired position ultrasonic imaging probe 6 when the ultrasonic imaging probe 6 was pointed towards the target region during imaging.

To that end, the system 2 is preferably configured to emit and/or provide positioning data or positioning feedback to the human operator tasked with positioning the second probe.

For example, visual indications (e.g. a graphical indication of the current position of the therapeutic ultrasonic probe 4 and a graphical indication of the target position of the therapeutic ultrasonic probe) may be displayed graphically or visually on a graphical user interface on a graphical display of the interface 26. In some implementations, the graphical feedback can be displayed to the operator through a computer-assisted surgery system.

In another example, an auditory feedback can be emitted by a sound emitting device of the interface 26, depending on the difference between the current position of the therapeutic ultrasonic probe 4 and the target position of the therapeutic ultrasonic probe 4. For example, the emitted sound may change as the operator moves the therapeutic ultrasonic probe 4 closer to the target position (e.g. a parameter such as the pitch or the loudness or the repetition frequency of the emitted sound may change).

In yet another example, a haptic feedback can be provided to the user, to indicate the difference between the current position of the therapeutic ultrasonic probe and the target position of the therapeutic ultrasonic probe. The haptic feedback may, for example, include vibrations of the body of the therapeutic ultrasonic probe 4. The vibrations may be generated by a controllable haptic feedback device, such as a vibrator, or a piezoelectric actuator, or any suitable technology, attached to or included in the body of the therapeutic ultrasonic probe 4.

Several feedback methods can be combined (e.g. visual feedback and auditory feedback) to provide a better feedback to the operator.

In preferred embodiments, the position capture system 10 is an optical position capture system. In that case, the position markers are optical position markers and the sensor (s) 12 of the position capture system 10 are image sensors, such as cameras.

The optical position markers can be passive optical markers (e.g. reflective markers, such as coated rubber balls illuminated by a light source of the position capture system 10, or simple visual markings) or active optical markers (e.g. illuminated markers comprising a light source).

For example, the position capture system 10 is a motion capture system.

The position capture system 10 is connected to and in communication with the electronic control device 8.

In alternative embodiments, the position capture system 10 is a magnetic position capture system. In that case, the position markers are magnetic position markers and the sensor(s) 12 of the position capture system 10 are magnetic sensors.

In other alternative embodiments, the position capture system 10 is a radiofrequency position capture system. In that case, the position markers are radiofrequency position markers (e.g. antennas, and preferably passive antennas) and the sensor(s) 12 of the position capture system 10 are radiofrequency sensors.

Other embodiments based on other position capture technologies or combinations of these position capture technologies can also be used without departing form the scope of the invention.

Figure 2:
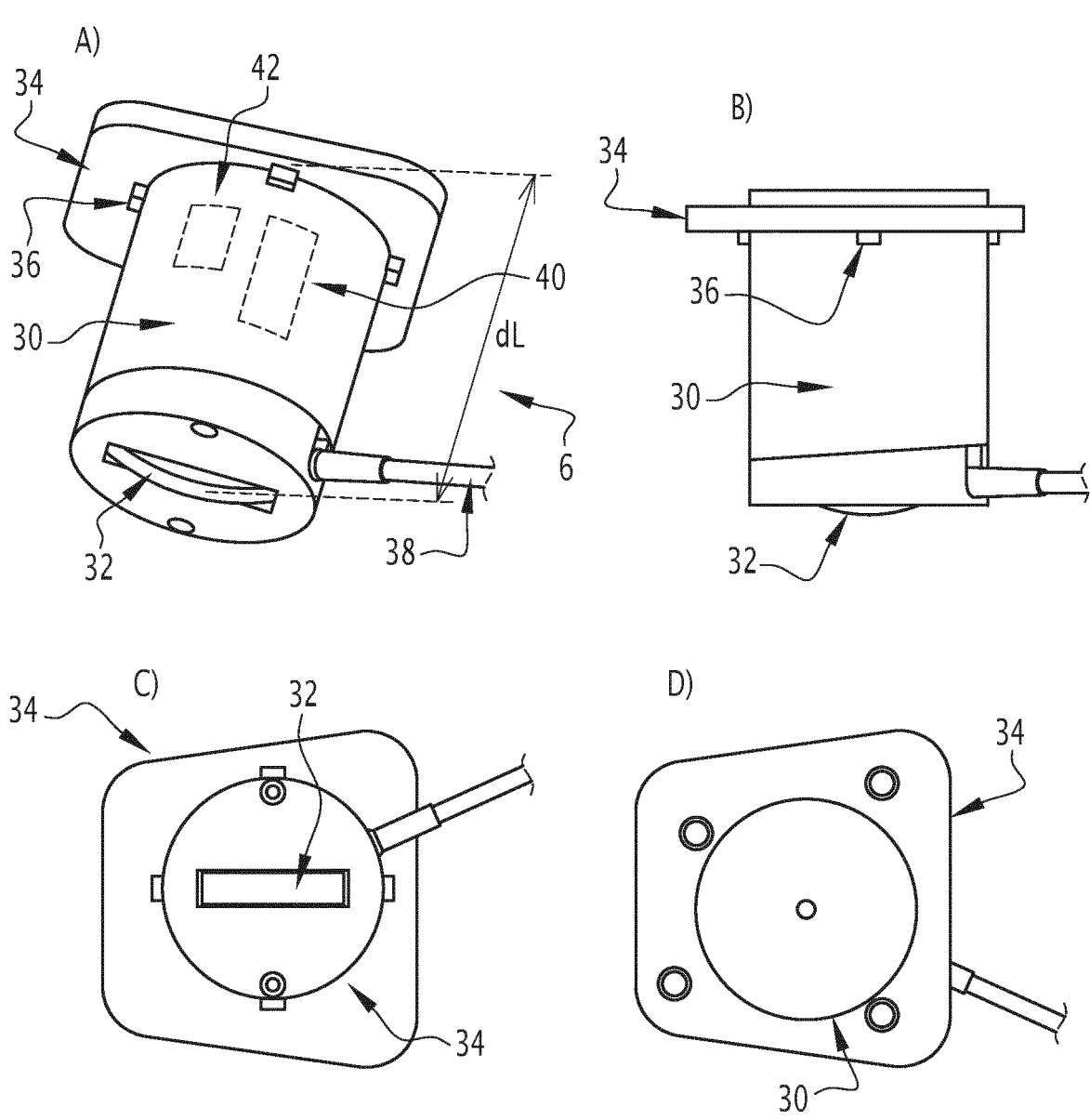
FIG. 2 is a simplified diagram of an embodiment of an enclosure for an ultrasonic imaging probe of the system of FIG. 1.

An example of housing of the imaging ultrasonic probe 6 is described in reference to FIG. 2. On the insert A) of FIG. 2, the housing of the imaging ultrasonic probe 6 is illustrated in an isometric perspective view. On the inserts B), C) and D) of FIG. 2, the same housing is illustrated respectively in a side view, in a bottom view and in a top view.

In many embodiments, the housing, or enclosure (or casing) comprises a body 30 defining a closed reception space in which the imaging probe 6 can be received.

The body 30 comprises an opening 32 configured to allow an active portion (e.g. a sensor portion or transducer portion) of the imaging ultrasonic probe 6, so that the probe 6 can image the target region while being inside the housing. For example, the opening 32 is formed on a lower portion of the body 30.

In the illustrated example, the body 30 has a cylindrical shape or tubular shape, other examples being possible.

For example, the height "dL" of the body 30 is comprised between 2 cm and 30 cm.

In this example, the housing comprises a flat top portion 34, or top lid, which closes the upper end of the body 30.

Positions markers 36 are placed on the body 30 (and attached to the body 30), preferably at multiple positions around the body 30, so as to be detectable by the position capture system 10 regardless of the orientation of the housing.

In the illustrated example, position markers 36 are attached to the lower surface of the top lid 34, although other configurations are possible.

The body 30 may be shaped so as to facilitate the attachment of the position markers 36. For example, a pre-built ring shaped position marker 36 can be received in a circular reception groove formed around the body 30.

An opening may be provided in the body 30 to allow the passage of a cable 38 for connecting the imaging ultrasonic probe 6 to the electronic control device 8.

In many embodiments, the housing is made of a biocompatible material. For example, the housing is made of stainless steel. In another example, the housing is made of a plastic material.

According to embodiments of the invention, the external dimensions of the housing are similar (and preferably identical) to the external dimensions of the therapeutic ultrasonic probe 4.

For example, the body 30 (and the housing as a whole) have a similar or identical shape and dimensions as the outer shape and dimensions of the therapeutic ultrasonic probe 4. In other words, the body 30 (and the housing as a whole) have a similar or identical height, and/or diameter and/or form factor and/or volume as the therapeutic ultrasonic probe 4.

Thus, the detection system perceives the imaging ultrasonic probe 6 to have the same shape and size (or a similar shape and size) as the therapeutic ultrasonic probe 4. This makes it easier to compare the position of the therapeutic ultrasonic probe 4 with the recorded position of the imaging ultrasonic probe 6 without having to extrapolate in real time a position and/or an orientation or to compensate for any size and/or shape difference between the probes 4 and 6, which may be computationally intensive and prone to errors. The more the probes 4 and 6 are similar in shape and dimensions to each other, the easier it is to compare their positions, especially when the positions are displayed visually in the interface 26.

Preferably, the position markers of the therapeutic probe 4 are placed at the same relative positions as the position markers of the housing of the probe 6, as this facilitates the comparison even more.

A further benefit of these features is that, in embodiments in which the probes 4 and 6 are manually placed by a human operator, having probes 4 and 6 of similar or identical size makes it easier for a skilled operator to place the therapeutic ultrasonic probe 4 at the same position as the imaging ultrasonic probe 6 (e.g. due to muscle memory).

In some optional embodiments, the housing comprises a mobile element 40 configured to modify the size of the reception portion in which the imaging ultrasonic probe 6 is received. Thus, the size of the reception portion can be modified to accommodate imaging ultrasonic probes 6 of different sizes within a single housing.

In some optional embodiments, the housing and the imaging ultrasonic probes 6 have the same weight as the therapeutic ultrasonic probe 4. For example, the housing comprises a secondary reception portion 42 capable of receiving removable weights (e.g. metal weight elements), in order to modify the total weight of the housing. Having probes 4 and 6 of similar or identical weight makes it easier for a skilled operator to place the therapeutic ultrasonic probe 4 at the same position as the imaging ultrasonic probe 6 (e.g. due to muscle memory), for the reasons explained above.

Figure 3:
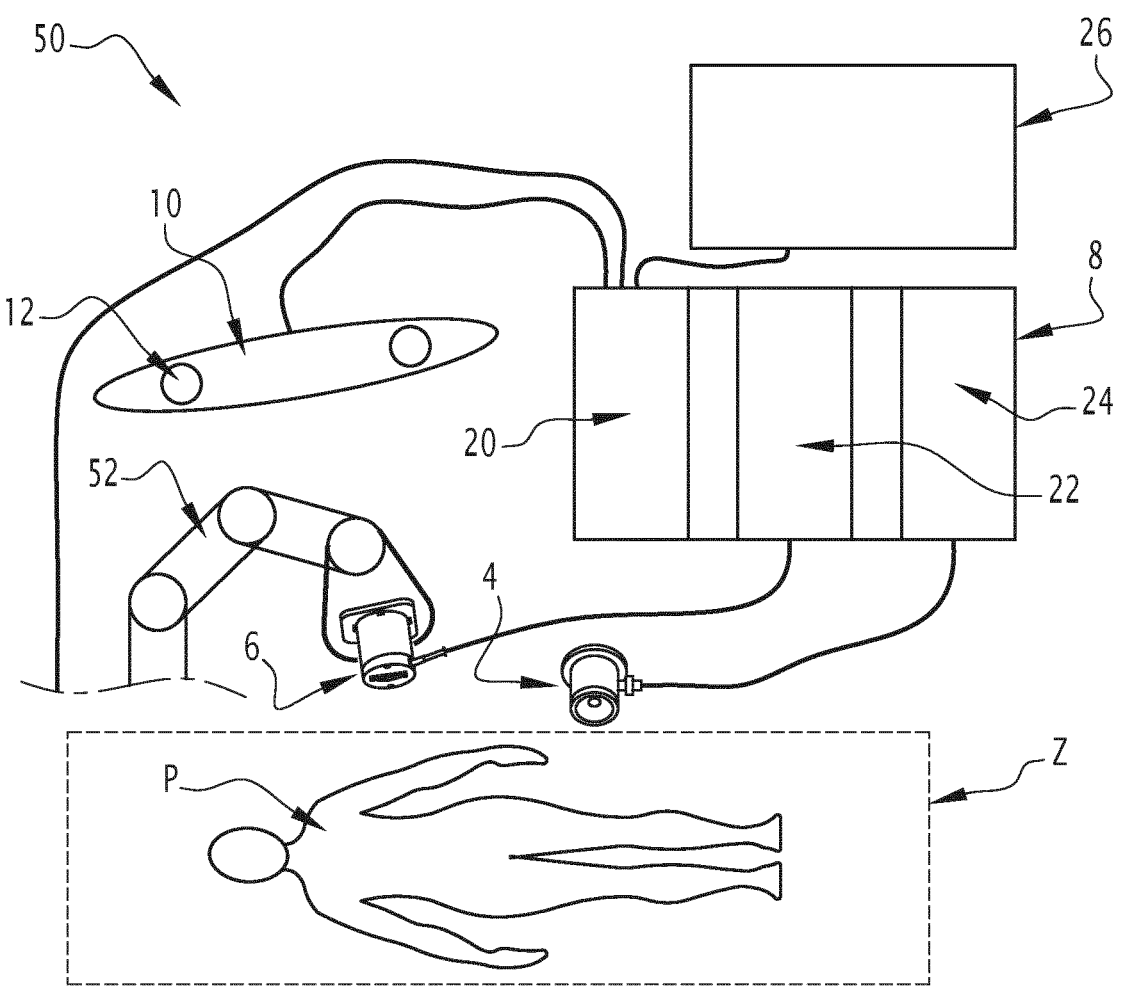
FIG. 3 is a simplified diagram of a system according to a first embodiment of the invention.

FIG. 3 illustrates another embodiment of the invention. A system 50 comprises a therapeutic ultrasonic probe 4, an imaging ultrasonic probe 6 placed inside a housing, an electronic control device 8 and a position capture system 10. The system 50 is similar to the system 2 and has a similar purpose. Hence, the description above made in reference to FIGS. 1 and 2 is largely applicable to the system 50 and will not be repeated.

The system 50 further comprises a robot 52, such as an industrial robot 52 configured to hold the imaging probe 6. For example, a free end of the robot 52 comprises a handling portion, such a clamp or a gripping tool, capable of holding the imaging probe 6. The robot 52 comprises one or more programmable actuators capable of moving the handling portion of the robot 52 (and the imaging probe 6 or the probe 4) to a desired position. An electronic controller of the robot 52 is capable of driving the actuator(s) and may be in communication with the electronic control device 8.

For example, the industrial robot 52 may be a SCARA robot, or a linear robot, or a Cartesian robot, or an articulated robot arm, or any equivalent industrial robot system. In some embodiments, the robot 52 may be a custom made robot, or more generally any mechanical system capable of automatically moving the handling portion (and the probe 4 or the probe 6) to a desired position.

In other words, in the embodiment of FIG. 3, the imaging ultrasonic probe 6 is positioned automatically using the industrial robot 52 instead on relying on a human operator to manually place the imaging ultrasonic probe 6 at the desired location. Positioning instructions (e.g. control signals and/or computer instructions) can be automatically sent to a controller of the industrial robot 52.

The imaging ultrasonic probe 6 can be placed at the desired location without the need for a continued and/or guided human-machine interaction process and thus without having to display graphical feedback and/or auditory feedback and/or haptic feedback or any combination thereof. Thus, in the embodiment of FIG. 3, the user interface 26 may be at least partially removed or omitted.

However, in some embodiments, the interface 26 may be used alongside the industrial robot 52, e.g. to provide positioning information to an operator supervising the operation of the industrial robot 52, even though the operator is not tasked with moving or positioning the probes 4 and 6.

The industrial robot 52 may also be configured to hold and position the therapeutic ultrasonic probe 4 at a desired location.

Figure 4:
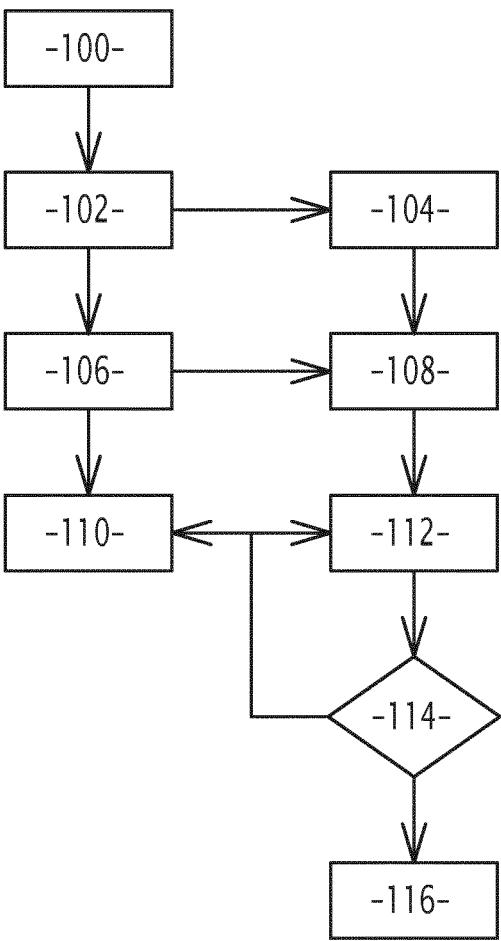
FIG. 4 is a simplified diagram of a method of operation of the system of FIG. 1 or FIG. 3 according to embodiments of the invention.

An example of operation, applicable to both the embodiments of system 2 and 50, is now described in reference to the diagram of FIG. 4.

Any flow charts, flow diagrams, state transition diagrams, pseudo code, and the like represent various processes which may be substantially represented in computer readable medium and executed by a computer or processor, e.g. by the electronic control device 8.

The method begins at block 100.

For example, the imaging ultrasonic probe 6 is acquired and held by an operator or by the industrial robot 52.

At block 102, the imaging ultrasonic probe 6 is placed at a first position, such as an imaging position, for example to acquire an image or an ultrasound mapping of a target region, e.g. in the subject P.

At block 104, the electronic control device 8 automatically acquires the position of the ultrasonic imaging probe 6 with the position capture system 10. The acquired position (e.g. a digital representation of the spatial position of one or more of the position markers in a three-dimensional space) may be recorded in a memory of the electronic control device 8.

At block 106, the imaging ultrasonic probe 6 is removed from the first position (e.g. removed from the imaging position) by the operator or by the industrial robot 52.

The therapeutic ultrasonic probe 4 is then acquired and held by the operator or by the industrial robot 52 and placed at a second position.

At block 108, the electronic control device 8 automatically detects the position of the therapeutic ultrasonic probe 4 using the position capture system 10.

At block 110, the operator or the industrial robot 52 moves the therapeutic ultrasonic probe 4 in order to reach the target position (the first position).

At block 112, the electronic control device 8 indicates the target position of the therapeutic ultrasonic probe based on the acquired position of the ultrasonic imaging probe.

The target position may be indicated along with the current position of the therapeutic ultrasonic probe 4. The current position may be updated in real time or at least periodically by the electronic control device 8 using the position capture system 10.

Depending on the embodiments, the target position (and eventually the difference between the target position and the current position) may be indicated in many different ways, such as control signals and instructions for the industrial robot 52, or as feedback for the human operator (in the form of visual feedback, and/or auditory feedback, and/or haptic feedback).

For example, at block 114, the electronic control device 8 compares the current position of the therapeutic ultrasonic probe 4, as measured by the position capture system 10, with the target position (the acquired first position).

If the current position of the therapeutic ultrasonic probe 4 matches the target position, then the method ends successfully (block 116). Otherwise, the method continues to run until a success is reached or until the method is aborted (by a user or after a timeout).

The detection of the markers allows to represent on the user interface the target position such as the user can place the therapeutic ultrasonic probe precisely at the target position. In particular, this allows to position also the ultrasound emission axis of the therapeutic ultrasonic probe 4 according in alignment with the ultrasound emission axis of the imaging ultrasonic probe 6, in other words, the emission axis target direction.

Other embodiments are possible.

For example, the method may comprise one or more additional steps for replacing the imaging ultrasonic probe 6 at the same location after the therapeutic ultrasonic probe 4 has been used, for example to image the area to image the target region after application of the ultrasound dose by the therapeutic ultrasonic probe 4. This may be used to confirm whether the probe 4 has delivered the appropriate therapeutic dose. Thus, the steps for positioning the imaging ultrasonic probe 6 are identical or similar to the steps described above for the therapeutic ultrasonic probe 4 (blocks 108 to 116)

For example, the therapeutic ultrasonic probe 4 is removed from the second position by the operator or by the industrial robot 52. The operator or the industrial robot 52 moves the imaging ultrasonic probe 6 in order to reach the target position.

The steps described above of detecting the position of the therapeutic ultrasonic probe 4 using the position capture system 10, moving the therapeutic ultrasonic probe 4 to reach the target position and indicating the target position of the therapeutic ultrasonic probe based on the acquired position of the ultrasonic imaging probe are repeated for the imaging ultrasonic probe 6.

In some other embodiments, the therapeutic ultrasonic probe 4 could be placed first (blocks 100 to 106 are modified in consequence to be applied to the therapeutic ultrasonic probe 4). Then, based on the determined target position, the system 2 or the system 50 is used to place the imaging ultrasonic probe 6 at the determined target position (blocks 108 to 116 are modified in consequence to be applied to the imaging ultrasonic probe 6).

In many alternative embodiments, the method steps described above could be executed in a different order. One or more method steps could be omitted or replaced by equivalent steps. Some method steps could be combined or dissociated into different method steps. The disclosed exemplary embodiment is not intended to be limiting and does not prevent other methods steps to be executed without departing from the scope of the claimed subject matter.

Owing to embodiments of the invention, the therapeutic ultrasonic probe 4 can be easily placed at the same position as the imaging ultrasonic probe 6 and aligned with the imaging ultrasonic probe 6, even though the therapeutic ultrasonic probe 4 and the imaging ultrasonic probe 6 are two distinct probes separate from each other.

In known systems, only compact and miniaturized imaging ultrasonic probe 6 could be used, since the only way to obtain a suitable alignment was to embed the imaging ultrasonic probe 6 in the therapeutic ultrasonic probe 4 with the same ultrasound emission axis. However, these compact and miniaturized imaging ultrasonic probe 6 have lower imaging capabilities due to their small size and cost requirements, among other reasons. Thus, in the embodiments of the invention, high quality imaging solutions can be used without compromising the positioning or alignment requirements.

The embodiments and alternatives described above may be combined with each other in order to create new embodiments of the invention within the scope of the claims.

The invention claimed is:

1. A method for positioning a therapeutic ultrasonic probe relative to an ultrasonic imaging probe, the method comprising, by an electronic control device:

acquiring a position of a first probe chosen among the ultrasonic imaging probe and the therapeutic ultrasonic probe, the position being acquired with a position capture system when the first probe is in a first position, the ultrasonic imaging probe being placed inside a housing, the housing comprising at least one position marker detectable by the position capture system, external dimensions of the housing being similar to external dimensions of the therapeutic ultrasonic probe, detecting a position of a second probe chosen among the other of the ultrasonic imaging probe and the therapeutic ultrasonic probe, the position being detected using the position capture system, the therapeutic ultrasonic probe comprising at least one position marker detectable by the position capture system, wherein the at least one position marker of the therapeutic ultrasonic probe is placed at relative positions that are the same as relative positions of the at least one position marker of the housing, indicating a target position of the second probe based on the acquired position of the first probe.

2. The method of claim 1, wherein the first probe is the ultrasonic imaging probe, wherein the second probe is the therapeutic ultrasonic probe, and wherein the first position is an imaging position.

3. The method of claim 1, wherein the first probe is the therapeutic ultrasonic probe, wherein the second probe is the ultrasonic imaging probe.

4. The method of claim 1, wherein each of the therapeutic ultrasonic probe and the ultrasonic imaging probe have an ultrasound emission axis, and wherein indicating the target position also comprises indicating a direction of the ultrasound emission axis.

5. The method according to claim 1, wherein the position capture system is configured to provide positioning data to an operator tasked with positioning the second probe.

6. The method of claim 5, wherein indicating the target position of the therapeutic ultrasonic probe comprises visually displaying a current position of the therapeutic ultrasonic probe and the target position of the therapeutic ultrasonic probe on a graphical user interface connected to the electronic control device.

7. The method of claim 5, wherein indicating the target position of the therapeutic ultrasonic probe comprises emitting an auditory feedback depending on a difference between the current position of the therapeutic ultrasonic probe and the target position of the therapeutic ultrasonic probe.

8. The method according to claim 5, wherein indicating the target position of the therapeutic ultrasonic probe comprises emitting a haptic feedback depending on a difference between the current position of the therapeutic ultrasonic probe and the target position of the therapeutic ultrasonic probe.

9. The method according to claim 1, wherein the therapeutic ultrasonic probe is held by a robot, and wherein indicating the target position of the therapeutic ultrasonic probe comprises sending position instructions to an electronic controller of the robot, the position instructions being configured to cause the robot to place the therapeutic ultrasonic probe at the target position.

10. A system for positioning a therapeutic ultrasonic probe relative to an ultrasonic imaging probe, comprising a therapeutic ultrasonic probe, an ultrasonic imaging probe placed inside a housing, a position capture system and an electronic control device, wherein external dimensions of the housing being similar to external dimensions of the therapeutic ultrasonic probe, wherein the housing comprises at least one position marker detectable by the position capture system, wherein the therapeutic ultrasonic probe comprises at least one position marker detectable by the position capture system, and wherein the electronic control device is configured to:

acquire a position of a first probe chosen among the ultrasonic imaging probe and the therapeutic ultrasonic probe with the position capture system when the first probe is in a first position, detect a position of a second probe chosen among the other of the ultrasonic imaging probe and the therapeutic ultrasonic probe, using the position capture system, indicate a target position of the second probe based on the acquired position of the first probe, wherein the at least one position marker of the therapeutic ultrasonic probe is placed at relative positions that are the same as relative positions of the at least one position marker of the housing.

11. The system of claim 10, wherein the ultrasonic imaging probe is received in a reception portion of the housing and wherein the housing comprises a mobile element configured to modify the size of the reception portion.

12. The system according to claim 10, wherein the housing comprises a secondary reception portion for receiving removable weights.

13. The system according to claim 10, wherein the housing is made of a biocompatible material.

14. The system according to claim 10, wherein the at least one position marker is at least one optical position marker, the position capture system comprising at least one image sensor.

15. A system for positioning a therapeutic ultrasonic probe relative to an ultrasonic imaging probe, comprising a therapeutic ultrasonic probe, an ultrasonic imaging probe placed inside a housing, a position capture system and an electronic control device, wherein external dimensions of the housing being similar to external dimensions of the therapeutic ultrasonic probe, wherein the housing comprises at least one position marker detectable by the position capture system, wherein the therapeutic ultrasonic probe comprises at least one position marker detectable by the position capture system, and wherein the electronic control device is configured to:

acquire a position of a first probe chosen among the ultrasonic imaging probe and the therapeutic ultrasonic probe with the position capture system when the first probe is in a first position, detect a position of a second probe chosen among the other of the ultrasonic imaging probe and the therapeutic ultrasonic probe, using the position capture system, indicate a target position of the second probe based on the acquired position of the first probe, wherein the housing comprises a secondary reception portion for receiving removable weights.

\* \* \* \* \*